(12) United States Patent
Watanabe (10) Patent No.: US 10,716,649 B2
(45) Date of Patent: Jul. 21, 2020

(54) POWDER MATERIAL FOR FORMING THREE-DIMENSIONAL OBJECT, MATERIAL SET FOR FORMING THREE-DIMENSIONAL OBJECT, METHOD FOR PRODUCING THREE-DIMENSIONAL OBJECT, THREE-DIMENSIONAL OBJECT PRODUCING APPARATUS, AND THREE-DIMENSIONAL OBJECT

(71) Applicant: Masaki Watanabe, Kanagawa (JP)

(72) Inventor: Masaki Watanabe, Kanagawa (JP)

(73) Assignee: Ricoh Company, Ltd., Tokyo (JP)

(*) Notice: Subject to any disclaimer, the term of this patent is extended or adjusted under 35 U.S.C. 154(b) by 314 days.

(21) Appl. No.: 15/705,624

(22) Filed: Sep. 15, 2017

(65) Prior Publication Data

US 2018/0000571 A1 Jan. 4, 2018

Related U.S. Application Data

(63) Continuation of application No. PCT/JP2016/050372, filed on Jan. 7, 2016.

(30) Foreign Application Priority Data

Mar. 16, 2015 (JP) .................................. 2015-052375

(51) Int. Cl.
*A61C 13/08* (2006.01)
*C04B 35/622* (2006.01)
(Continued)

(52) U.S. Cl.
CPC ................ *A61C 13/08* (2013.01); *A61C 5/77* (2017.02); *A61C 8/00* (2013.01); *A61C 13/00* (2013.01);
(Continued)

(58) Field of Classification Search
CPC ....... A61C 13/08; A61C 13/087; A61C 13/09; A61C 19/003; A61C 13/0018;
(Continued)

(56) References Cited

U.S. PATENT DOCUMENTS

| 8,475,946 B1 | 7/2013 | Dion et al. |
| 2004/0026807 A1 | 2/2004 | Andersson et al. |

(Continued)

FOREIGN PATENT DOCUMENTS

| EP | 2 516 351 A1 | 10/2012 |
| JP | 2003-531034 | 10/2003 |

(Continued)

OTHER PUBLICATIONS

Extended European Search Report dated Feb. 22, 2018 in Patent Application No. 16764512.6.

(Continued)

*Primary Examiner* — Stella K Yi
(74) *Attorney, Agent, or Firm* — Oblon, McClelland, Maier & Neustadt, L.L.P.

(57) ABSTRACT

Provided is a powder material for forming a three-dimensional object, the powder material containing granulated particles containing: a resin; and inorganic particles of which primary particles have a volume average particle diameter of 1 micrometer or less, wherein the granulated particles have a volume average particle diameter of 10 micrometers or greater but 70 micrometers or less and a BET specific surface area of 6 $m^2$/g or greater but 8 $m^2$/g or less.

20 Claims, 2 Drawing Sheets

(51) Int. Cl.

| | | |
|---|---|---|
| C08K 3/22 | (2006.01) | |
| B33Y 80/00 | (2015.01) | |
| B33Y 70/00 | (2020.01) | |
| B33Y 10/00 | (2015.01) | |
| B29C 67/00 | (2017.01) | |
| A61C 8/00 | (2006.01) | |
| A61C 13/00 | (2006.01) | |
| B28B 1/32 | (2006.01) | |
| A61C 13/083 | (2006.01) | |
| C04B 35/626 | (2006.01) | |
| C04B 35/634 | (2006.01) | |
| C04B 35/486 | (2006.01) | |
| A61K 6/16 | (2020.01) | |
| A61K 6/818 | (2020.01) | |
| A61K 6/822 | (2020.01) | |
| C04B 35/48 | (2006.01) | |
| B33Y 30/00 | (2015.01) | |
| A61C 5/77 | (2017.01) | |
| B29C 64/165 | (2017.01) | |
| C08L 101/00 | (2006.01) | |
| C08L 29/04 | (2006.01) | |
| C08K 7/00 | (2006.01) | |
| C08J 5/00 | (2006.01) | |
| C08L 33/02 | (2006.01) | |
| B29K 29/00 | (2006.01) | |
| B29K 33/00 | (2006.01) | |
| B29L 31/00 | (2006.01) | |

(52) U.S. Cl.
CPC ........ *A61C 13/0019* (2013.01); *A61C 13/083* (2013.01); *A61K 6/16* (2020.01); *A61K 6/818* (2020.01); *A61K 6/822* (2020.01); *B28B 1/32* (2013.01); *B29C 64/165* (2017.08); *B29C 67/00* (2013.01); *B33Y 10/00* (2014.12); *B33Y 30/00* (2014.12); *B33Y 70/00* (2014.12); *B33Y 80/00* (2014.12); *C04B 35/48* (2013.01); *C04B 35/486* (2013.01); *C04B 35/622* (2013.01); *C04B 35/62655* (2013.01); *C04B 35/62695* (2013.01); *C04B 35/63416* (2013.01); *C04B 35/63424* (2013.01); *C08K 3/22* (2013.01); *B29K 2029/04* (2013.01); *B29K 2033/08* (2013.01); *B29L 2031/7536* (2013.01); *C04B 2235/3217* (2013.01); *C04B 2235/3225* (2013.01); *C04B 2235/5296* (2013.01); *C04B 2235/5409* (2013.01); *C04B 2235/549* (2013.01); *C04B 2235/5436* (2013.01); *C04B 2235/608* (2013.01); *C04B 2235/6026* (2013.01); *C04B 2235/6581* (2013.01); *C04B 2235/76* (2013.01); *C04B 2235/96* (2013.01); *C08J 5/00* (2013.01); *C08K 7/00* (2013.01); *C08K 2003/221* (2013.01); *C08K 2003/2227* (2013.01); *C08K 2003/2244* (2013.01); *C08L 29/04* (2013.01); *C08L 33/02* (2013.01); *C08L 101/00* (2013.01)

(58) Field of Classification Search
CPC ....... A61C 13/0019; A61C 5/77; A61C 13/00; B33Y 10/00; B33Y 30/00; B33Y 70/00; B33Y 80/00; B29C 64/165; B29C 64/171; B29C 64/10; B29C 64/124; B29C 64/153; C04B 35/622
See application file for complete search history.

(56) References Cited

U.S. PATENT DOCUMENTS

| | | |
|---|---|---|
| 2005/0027050 A1 | 2/2005 | Monsheimer et al. |
| 2006/0223928 A1 | 10/2006 | Monsheimer et al. |
| 2008/0172951 A1 | 7/2008 | Starling |
| 2010/0025874 A1 | 2/2010 | Apel et al. |
| 2012/0094579 A1 | 4/2012 | Starling |
| 2012/0326361 A1 | 12/2012 | Bocciarelli et al. |
| 2013/0171416 A1* | 7/2013 | Diekmann ............ C08G 69/14 428/156 |
| 2013/0177767 A1 | 7/2013 | Grebe et al. |
| 2015/0259247 A1 | 9/2015 | Watanabe |
| 2015/0315086 A1 | 11/2015 | Kawamura et al. |
| 2016/0038633 A1 | 2/2016 | Watanabe |
| 2016/0236412 A1 | 8/2016 | Kusahara et al. |

FOREIGN PATENT DOCUMENTS

| | | |
|---|---|---|
| JP | 2005-048186 | 2/2005 |
| JP | 2006-076822 | 3/2006 |
| JP | 2006-143551 A | 6/2006 |
| JP | 2006-321711 | 11/2006 |
| JP | 2006-528717 | 12/2006 |
| JP | 2010-031011 | 2/2010 |
| JP | 2010-229170 | 10/2010 |
| JP | 2011-021218 | 2/2011 |
| JP | 2013-141830 | 7/2013 |
| WO | WO 2014/104236 A1 | 7/2014 |
| WO | WO 2015/046629 A1 | 4/2015 |

OTHER PUBLICATIONS

International Search Report dated Mar. 15, 2016 for counterpart International Patent Application No. PCT/JP2016/050372 filed Jan. 7, 2016 (with English Translation).
Written Opinion dated Mar. 15, 2016 for counterpart International Patent Application No. PCT/JP2016/050372 filed Jan. 7, 2016.
Official Communication dated Apr. 15, 2020 issued in corresponding European patent application No. 16 764 512.6.
Gu et al—"Laser additive manufacturing of metallic components: materials, processes and mechanisms", International Materials Reviews, vol. 57, No. 3, May 1, 2012, pp. 133-164.
Wong et al.—"A Review of Additive Manufacturing", ISRN Mechanical Engineering, vol. 47, No. 9, Jan. 1, 2012, 10 pages.
Murr et al.—"Next-generation biomedical implants using additive manufacturing of complex, cellular and functional mesh arrays", Philosophical Transactions of the Royal Society, vol. 368, Mar. 22, 2010, pp. 1999-2032.
Syed et al—"Combining wire and coaxial powder feeding in laser direct metal deposition for rapid prototyping", Applied Surface Science, vol. 252, No. 13, Apr. 30, 2006, pp. 4803-4808.

* cited by examiner

POWDER MATERIAL FOR FORMING THREE-DIMENSIONAL OBJECT, MATERIAL SET FOR FORMING THREE-DIMENSIONAL OBJECT, METHOD FOR PRODUCING THREE-DIMENSIONAL OBJECT, THREE-DIMENSIONAL OBJECT PRODUCING APPARATUS, AND THREE-DIMENSIONAL OBJECT

CROSS-REFERENCE TO RELATED APPLICATIONS

The present application is a continuation application of International Application No. PCT/JP2016/050372, filed Jan. 7, 2016, which claims priority to Japanese Patent Application No. 2015-052375, filed Mar. 16, 2015. The contents of these applications are incorporated herein by reference in their entirety.

BACKGROUND OF THE INVENTION

Field of the Invention

The present disclosure relates to a powder material for forming a three-dimensional object, a material set for forming a three-dimensional object, a method for producing a three-dimensional object, a three-dimensional object producing apparatus, and a three-dimensional object.

Description of the Related Art

Hitherto, prostheses for teeth (for example, artificial teeth) have been formed of metal materials such as cobalt-chromium alloys, ceramic materials such as zirconia, and organic materials such as hybrid resins combined with fillers, and have been used. Artificial teeth work in place of a dysfunctional occlusal function. Many of the materials for artificial teeth not only undergo temporal changes such as wear and corrosion, but also have aesthetic problems such as stronger whiteness than natural teeth. For example, zirconia has been known as a material expected to overcome this problem. Zirconia has transparency and, with addition of a color gradation, can form artificial teeth that do not look different when placed beside natural teeth. In order to be handled as prostheses, zirconia needs processing to be formed into desired shapes. However, zirconia, which is an extremely hard material, not only takes a lot of time, but also cannot be finely processed in a manner to include an internal structure, particularly in the case of cutting by CAD/CAM.

Meanwhile, powder additive manufacturing is expected to enable fine processing intended for inclusion of an internal structure, and methods using lasers and electron beams have been proposed (see, for example, Japanese Translation of PCT International Application Publication No. JP-T-2003-531034 and Japanese Unexamined Patent Application Publication No. 2011-21218).

SUMMARY OF THE INVENTION

According to one aspect of the present disclosure, a powder material for forming a three-dimensional object contains granulated particles containing: a resin; and inorganic particles of which primary particles have a volume average particle diameter of 1 micrometer or less. The granulated particles have a volume average particle diameter of 10 micrometers or greater but 70 micrometers or less and a BET specific surface area of 6 $m^2/g$ or greater but 8 $m^2/g$ or less.

DESCRIPTION OF THE EMBODIMENTS (Powder Material for Forming Three-Dimensional Object)

A powder material for forming a three dimensional object of the present disclosure (may also be referred to as "powder material for additive manufacturing") contains granulated particles and further contains other components as needed.

The powder material for forming a three-dimensional object of the present disclosure is based on that: existing powder additive manufacturing cannot use zirconia for forming a three-dimensional object, because zirconia has an extremely high melting point and cannot be sintered with, for example, a typical laser.

The present disclosure has an object to provide a powder material for forming a three-dimensional object capable of forming a three-dimensional object that is formed of particles having a high melting point and a high hardness and has a complicated three-dimensional shape easily, efficiently, with a high strength, and rapidly.

The present disclosure can provide a powder material for forming a three-dimensional object capable of forming a three-dimensional object that is formed of particles having a high melting point and a high hardness and has a complicated three-dimensional shape easily, efficiently, with a high strength, and rapidly.

<Granulated Particles>

The granulated particles are particles obtained by granulating a resin and inorganic particles.

The volume average particle diameter of the granulated particles is 10 micrometers or greater but 70 micrometers or less and preferably 30 micrometers or greater but 50 micrometers or less. When the volume average particle diameter of the granulated particles is 10 micrometers or greater, the powder material will have a favorable fluidity and can be easily supplied from a supplying-side powder storing tank during object formation. On the other hand, when the volume average particle diameter of the granulated particles is 70 micrometers or less, the particles will have appropriate gaps after formed into an object and shrink a little when sintered, leading to a favorable dimensional precision.

The volume average particle diameter of the granulated particles can be measured with a known particle size measuring instrument such as MULTISIZER III (available from Coulter Counter, Inc.) or FPIA-3000 (available from Sysmex Corporation) according to a known method.

The BET specific surface area of the granulated particles is 6.0 $m^2/g$ or greater but 8.0 $m^2/g$ or less and preferably 6.5 $m^2/g$ or greater but 7.5 $m^2/g$ or less. When the BET specific surface area of the granulated particles is 6.0 $m^2/g$ or greater, the amount of the resin encapsulated will be appropriate and the amount of the resin to be eluted during object formation will be appropriate. This provides an object (green body) with a favorable mechanical strength and enables object formation in a desired shape. On the other hand, when the BET specific surface area of the granulated particles is 8.0 m²/g or less, the granulated particles have an appropriate concave-convex condition on the outermost surface to have a favorable fluidity, enable smooth powder conveyance during object formation, and enable object formation in a desired shape.

The average circularity of the granulated particles represented by a formula below is preferably 0.960 or greater and more preferably 0.980 or greater.

Average circularity=(perimeter of a circle having the same area as a projected area of a particle/perimeter of a projected image of a particle)×100

When the average circularity of the granulated particles is 0.960 or greater, a filling rate at which a thin film formed of the granulated particles is filled with the granulated particles will be sufficient, to generate no voids. This makes it possible to prevent generation of, for example, voids in the object to be obtained.

The average circularity can be measured with a known circularity measuring instrument such as FPIA-3000 (available from Sysmex Corporation) according to a known method.

The untamped density of the granulated particles is 1.00 g/cm³ or greater but 1.40 g/cm³ or less and more preferably 1.10 g/cm³ or greater but 1.30 g/cm³ or less. When the untamped density of the granulated particles is 1.00 g/cm³ or greater but 1.40 g/cm³ or less, the powder material will have a favorable fluidity, enable powder conveyance safely during object formation, and facilitate object formation in a desired shape.

The tamped density of the granulated particles is preferably 1.20 g/cm³ or greater but 1.60 g/cm³ or less and more preferably 1.30 g/cm³ or greater but 1.50 g/cm³ or less. When the tamped density of the granulated particles is 1.20 g/cm³ or greater but 1.60 g/cm³ or less, the powder material will have a favorable fluidity, enable powder conveyance safely during object formation, and facilitate object formation in a desired shape.

The untamped density and the tamped density can be measured with, for example, a powder tester (available from Tsutsui Scientific Instruments Co., Ltd.).

The rate of mass reduction from before to after the granulated particles are heated at 1,000 degrees C. for 1 hour is preferably 5% by mass or less. When the rate of mass reduction is 5% by mass or less, it is possible to suppress adverse influence to crystallization due to a sintering residue, or to suppress crack generation.

The rate of mass reduction can be measured with, for example, a simultaneous thermogravimetric-differential thermal analyzer (available from SII Nanotechnology Inc., TG-DTA 6200 EXSTAR 6000).

<<Inorganic Particles>>

The material of the inorganic particles is not particularly limited and may be appropriately selected depending on the intended purpose. Examples of the material of the inorganic particles include zirconia, alumina, and silica. One of these materials may be used alone or two or more of these materials may be used in combination. Among these materials, zirconia is preferable.

When zirconia is used for the inorganic particles, for example, yttria serving as a sintering aid and alumina serving as an impurity may be added.

Zirconia has an extremely high melting point. Therefore, even if zirconia is used for three-dimensional object formation by an inkjet method, zirconia cannot be sintered unless the primary particle diameter of zirconia is small, making it impossible to ensure a sufficient mechanical strength. An ideal primary particle diameter is on the order of some hundreds of nanometers or less. When the primary particle diameter is 1 micrometer or greater, it is almost safe to consider that particles cannot be sintered. However, there is a need for conveying the powder from a supplying-side powder storing tank to a forming-side powder storing tank for performing three-dimensional object formation by an inkjet method. If the size of the particles constituting the powder is small, there occurs a strong interparticle force, which may significantly degrade fluidity. Therefore, in order to improve fluidity while maintaining sinterability, there is a need for granulating (aggregating) particles while maintaining the primary particle diameter to the order of some hundreds of nanometers and making the particle diameter have increased to the micro order when granulation is completed.

In the case of employing the inkjet method, there is a three-dimensional object forming method of laminating powder material layers while adding a resin, as described above. However, in the case of existing three-dimensional object forming methods, there are often cases where the surface of the particles is coated with the resin. If coating is applied to primary particles of the nano-order, a powder having a significantly poor fluidity is obtained, as described above. Therefore, it is desirable to establish a technique for granulating particles while adding a binding agent and maintaining the primary particle diameter to the nano-order, and growing the particles to the micro-order.

The volume average particle diameter of the primary particles of the inorganic particles is 1 micrometer or less. When the volume average particle diameter of the primary particles is 1 micrometer or less, zirconia sufficiently dissolves when fired, and can be sintered easily.

The volume average particle diameter of the inorganic particles can be measured with a known particle size measuring instrument such as MULTISIZER III (available from Coulter Counter, Inc.) or FPIA-3000 (available from Sysmex Corporation) according to a known method.

The content of zirconia in the inorganic particles is 90% by mass or greater and more preferably 94% by mass or greater. When the content of zirconia is 90% by mass or greater, the relative amount of the sintering aid or the impurity is low. This provides an excellent mechanical strength and prevents discoloring.

The content of yttria in the inorganic particles is preferably 2% by mass or greater but 6% by mass or less and more preferably 3% by mass or greater but 5% by mass or less. In the yttria content range of 2% by mass or greater but 6% by mass or less, the function as a sintering aid is sufficiently exerted, and a crack is not generated during firing.

The content of alumina in the inorganic particles is preferably 3% by mass or less and more preferably 1% by mass or less. When the content of alumina is 3% by mass or less, the function as a sintering aid is favorable, and an adverse influence is not imparted to color.

The contents of zirconia, yttria, and alumina in the inorganic particles can be measured by, for example, an ICP emission spectrophotometric method.

The monoclinic rate of the inorganic particles is preferably 30% by mass or less and more preferably 20% by mass or less. When the monoclinic rate of the inorganic particles is 30% by mass or less, the tetragonal rate is appropriate and a mechanical strength is favorable.

The monoclinic rate of the inorganic particles can be measured with, for example, an X-ray powder diffractometer under predetermined conditions.

The method for producing the inorganic particles is not particularly limited and may be appropriately selected depending on the intended purpose. Examples of the method include a pyrolysis method, a coprecipitation method, a hydrolysis method, and a method for synthesizing inorganic particles from a metal salt aqueous solution of zirconia and yttria. Among these methods, the pyrolysis method or the coprecipitation method is preferable.

In the pyrolysis method, predetermined amounts of zirconium oxychloride and an yttrium chloride aqueous solution are mixed. To the resultant, sodium chloride (or potassium chloride) is added in an amount of from 0.1% by mass through 1% by mass of the amount of zirconium oxychloride and mixed. The mixture liquid is subjected to instantaneous drying by, for example, a spray drying method, to obtain a dry powder.

The instantaneous drying is a method that can dry the target within 10 seconds. It is preferable to perform drying at a drying temperature of 200 degrees C. or higher in heated air.

Next, the dry powder is pyrolyzed in the air at a temperature of 800 degrees C. or higher but 1,200 degrees C. or lower, to obtain an oxide calcined powder. The oxide calcined powder is pulverized by a wet grinding method to a pulverization diameter of 2 micrometers or less, and washed with water. The method for washing with water is not particularly limited and may be appropriately selected depending on the intended purpose. A continuous washing filtration method using a membrane filter is preferable.

Washing with water is performed sufficiently in a manner that by washing with water, the sodium (or potassium) concentration in the inorganic particles falls within a range of 10 ppm or greater but 100 ppm or less as an oxide equivalent amount. The slurry obtained from washing with water is dried, to obtain inorganic particles (zirconia powder).

In the coprecipitation method, zirconium oxychloride and an yttrium chloride aqueous solution are mixed. Here, particularly, in order to form a metal complex in a manner to make hydrates of zirconium oxychloride and yttrium chloride precipitate at the same pH, sodium sulfate (or potassium sulfate) is added at a ratio by mole of 0.3 or greater but 0.7 or less relative to zirconia and is allowed to undergo a reaction at a temperature of 50 degrees C. or higher but 100 degrees C. or lower for some hours or longer. To this mixture liquid, an alkali aqueous solution of, for example, sodium hydroxide or ammonia is added under stirring, to adjust pH of the aqueous solution to 8 or higher but 10 or lower. The obtained particles of the coprecipitated hydrates are sufficiently washed with water, and it is confirmed that sodium (or potassium) is in the range of from 10 ppm or greater but 100 ppm or less as an oxide equivalent. The particles of the hydrates after washed with water are dehydrated and dried, and fired in the air at a temperature of 800 degrees C. or higher but 1,200 degrees C. or lower, to obtain an oxide calcined powder. The obtained oxide calcined powder is pulverized by a wet method to 2 micrometers or less and dried, to obtain inorganic particles (zirconia powder).

<<Resin>>

As the resin, a water-soluble resin is preferable for use.

Water-solubility of the water-soluble resin means that the resin dissolves in water in an amount of 10% by mass or greater at room temperature (25 degrees C.).

As the resin, a resin containing an acidic functional group is preferable. Examples of such a resin include a polyvinyl alcohol and a polyacrylic acid. Of these resins, a polyacrylic acid having the higher acidity is preferable.

The weight average molecular weight Mw of the polyacrylic acid is preferably 500,000 or greater but 1,000,000 or less and more preferably 600,000 or greater but 900,000 or less. When the weight average molecular weight Mw of the polyacrylic acid is 500,000 or greater, the polyacrylic acid can easily form a cross-linked structure with a liquid material for forming an object, and a hardening time for the object will be appropriate. On the other hand, when the weight average molecular weight Mw of the polyacrylic acid is 1,000,000 or less, a slurry viscosity will be appropriate, an aqueous solution of the polyacrylic acid can be supplied favorably during spray dry granulation, and there will be no variation in the granulated particles to be obtained.

The weight average molecular weight Mw of the polyacrylic acid can be calculated based on a molecular weight distribution of the polyacrylic acid isolated by, for example, a gel permeation chromatography (GPC) method.

The method for adding the resin to the inorganic particles is not particularly limited and may be appropriately selected depending on the intended purpose. Examples of the method include a method of adding the resin at a timing of granulation by spray drying so that the resin is supported even inside aggregates (secondary particles) of the inorganic particles.

The amount of the resin added to the inorganic particles is preferably 0.1% by mass or greater but 5% by mass or less and more preferably 0.5% by mass or greater but 3% by mass or less. When the amount of the resin added is 0.1% by mass or greater, a cross-linking reaction will occur appropriately and an object will have a favorable strength. On the other hand, when the amount of the resin added is 5% by mass or less, an object after sintered will have a favorable mechanical strength.

The amount of the resin added can be measured with a known thermal analyzer such as DSC-200 (available from Seiko Instruments Inc.) according to a known method.

<Other Components>

The other components that can be contained in the powder material are not particularly limited and may be appropriately selected depending on the intended purpose. Examples of the other components include a fluidizer, a filler, a leveling agent, and a sintering aid.

It is preferable that the powder material for forming a three-dimensional object contain the fluidizer, because, for example, a layer of the powder material can be formed easily and efficiently. It is preferable that the powder material for forming a three-dimensional object contain the filler, because it is less likely that, for example, voids will be generated in a hardened product (three-dimensional object, hardened product for sintering) to be obtained. It is preferable that the powder material for forming a three-dimensional object contain the leveling agent, because, for example, handling is facilitated. It is preferable that the powder material for forming a three-dimensional object contain the sintering aid, because a hardened product (three-dimensional object, additively manufactured object, hardened product for sintering) obtained can be sintered at a lower temperature in a sintering treatment.

The powder material for forming a three-dimensional object can be favorably used for easy, efficient production of various three-dimensional objects and structures, and can be particularly favorably used for a method for producing a three-dimensional object and a three-dimensional object producing apparatus of the present disclosure to be described below.

(Material Set for Forming Three-Dimensional Object)

A material set for forming a three-dimensional object of the present disclosure (may also be referred to as "material set for additive manufacturing") includes the powder material for forming a three-dimensional object of the present disclosure and a liquid material for forming a three-dimensional object (may also be referred to as "liquid material for additive manufacturing"), and further includes other components as needed.

<Liquid Material for Forming Three-Dimensional Object>

The liquid material for forming a three-dimensional object contains an aqueous medium and further contains other components as needed.

Aqueous Medium

Examples of the aqueous medium include water, alcohol such as ethanol, and ether, and ketone. Water is preferable. Water in which a component other than water, such as the alcohol is contained in a small amount may also be used as the aqueous medium.

Examples of the water include pure water such as ion-exchanged water, ultrafiltrated water, reverse osmotic water, and distilled water, and ultrapure water.

Other Components

Examples of the other components include a cross-linking agent, a preservative, an antiseptic, a stabilizer, and a pH adjuster.

The cross-linking agent is not particularly limited and may be appropriately selected depending on the intended purpose. Examples of the cross-linking agent include polyethyleneimine.

The material set for forming a three-dimensional object of the present disclosure can be favorably used for easy, efficient production of various compacts and structures, and can be particularly favorably used for a method for producing a three-dimensional object and a three-dimensional object producing apparatus of the present disclosure to be described below.

(Method for Producing Three-Dimensional Object and Three-Dimensional Object Producing Apparatus)

A method for producing a three-dimensional object of the present disclosure includes at least a layer forming step, preferably includes a liquid material applying step and a sintering step, and further includes other steps as needed.

A three-dimensional object producing apparatus of the present disclosure includes at least a layer forming unit, preferably includes a liquid material applying unit and a sintering unit, and further includes other units as needed.

The method for producing a three-dimensional object of the present disclosure can be favorably performed with the three-dimensional object producing apparatus of the present disclosure. The layer forming step can be favorably performed by the layer forming unit. The liquid material applying step can be favorably performed by the liquid material applying unit. The sintering step can be favorably performed by the sintering unit. The other steps can be favorably performed by the other units.

<Layer Forming Step and Layer Forming Unit>

The layer forming step is a step of forming a layer of the powder material for forming a three-dimensional object of the present disclosure on a support, the layer having a predetermined thickness.

The layer forming unit is a unit configured to form a layer of the powder material for forming a three-dimensional object of the present disclosure on a support, the layer having a predetermined thickness.

Support

The support is not particularly limited and may be appropriately selected so long as the powder material can be placed on the support. Examples of the support include a table having a placing surface on which the powder material is placed, and a base plate of the apparatus illustrated in FIG. 1 of Japanese Unexamined Patent Application Publication No. 2000-328106. The surface of the support, i.e., the placing surface on which the powder material is placed may be a smooth surface, a coarse surface, a planar surface, or a curved surface.

Formation of Layer of Powder Material for Forming Three-Dimensional Object

The method for placing the powder material on the support is not particularly limited and may be appropriately selected depending on the intended purpose. Examples of a method for placing the powder material as a thin layer include a method using a known counter rotating mechanism (counter roller) employed in a selective laser sintering method described in Japanese Patent No. 3607300, a method for spreading the powder material to have a form of a thin layer with such a member as a brush, a roller, and a blade, a method for pressing the surface of the powder material with a pressing member to spread the powder material to have a form of a thin layer, and a method using a known powder additive manufacturing apparatus.

The following procedure may be followed to place the powder material on the support as a thin layer with, for example, the counter rotating mechanism (counter roller), the brush, the roller, or the blade, or the pressing member. That is, with, for example, the counter rotating mechanism (counter roller), the brush, the roller, or the blade, or the pressing member, the powder material is placed on the support that is disposed within an outer frame (may also be referred to as, for example, "mold", "hollow cylinder", or "tubular structure") in a manner that the support can lift upward and downward while sliding against the inner wall of the outer frame. When the support used is a support that can lift upward and downward within the outer frame, the support is disposed at a position slightly lower than the upper-end opening of the outer frame, i.e. at a position lower by an amount corresponding to the thickness of a layer of the powder material, and then the powder material is placed on the support. In this way, the powder material can be placed on the support as a thin layer.

When a laser, an electron beam, or the liquid material by an inkjet method is caused to act on the powder material placed as a thin layer in the way described above, hardening occurs. When the powder material is placed as a thin film on the obtained hardened product of the thin layer in the same way as described above and a liquid, an electron beam, or the liquid material is caused to act on the (layer of) the powder material placed as a thin layer, hardening occurs. This hardening occurs not only in the (layer of) the powder material placed as a thin layer, but also between this layer of the powder material and the underlying hardened product of the thin layer obtained in the earlier hardening. As a result, a hardened product (three-dimensional object, additively manufactured object, hardened product for sintering) having a thickness corresponding to about two layers of the powder material placed as a thin layer is obtained.

An automatic simple method using the known powder additive manufacturing apparatus can also be employed in order to place the powder material as a thin layer on the support. The powder additive manufacturing apparatus typically includes a recoater configured to laminate layers of the powder material, a supplying-side powder storing tank configured to supply the powder material onto the support, and a forming-side powder storing tank in which the powder material is placed as thin layers and laminated. In the powder additive manufacturing apparatus, it is possible to constantly place the surface of the supplying-side powder storing tank at a height slightly higher than the surface of the forming-side powder storing tank, by lifting the supplying-side powder storing tank upward, lifting the forming-side powder storing tank downward, or both, it is possible to actuate the recoater from the supplying-side powder storing tank side and place the powder material as a thin layer, and it is also possible to laminate thin layers of the powder material by repeatedly moving the recoater.

The average thickness of a layer of the powder material is not particularly limited and may be appropriately selected depending on the intended purpose. For example, an average thickness per layer is preferably 3 micrometers or greater but 200 micrometers or less and more preferably 10 micrometers or greater but 100 micrometers or less. When the average thickness of a layer is 3 micrometers or greater, a time taken until an object can be obtained will be appropriate, and problems such as a shape collapse will not occur during treatment such as sintering or during handling. When the average thickness of a layer is 200 micrometers or less, an object can be provided with a sufficient dimensional precision.

The average thickness can be measured according to a known method.

<Liquid Material Applying Step and Liquid Material Applying Unit>

The liquid material applying step is a step of applying the liquid material for forming a three-dimensional object containing an aqueous medium to the layer of the powder material for forming a three-dimensional object.

The liquid material applying unit is a unit configured to apply the liquid material for forming a three-dimensional object containing an aqueous medium to the layer of the powder material for forming a three-dimensional object.

The method for applying the liquid material containing the aqueous medium to the layer of the powder material is not particularly limited and may be appropriately selected depending on the intended purpose. Examples of the method include a dispenser method, a spray method, and an inkjet method. Known apparatuses can be favorably used as the liquid material applying unit to carry out these methods. Among these methods, the dispenser method has an excellent liquid droplet quantitativity, but has a small coating coverage. The spray method can form a minute discharged material easily and has a wide coating coverage and an excellent coatability, but has a poor liquid droplet quantitativity and causes powder scattering due to a spray current. Hence, in the present disclosure, the inkjet method is particularly preferable. The inkjet method is preferable because the inkjet method is better than the spray method in liquid droplet quantitativity, can obtain a greater coating coverage than can be obtained by the dispenser method, and can form a complicated three-dimensional shape with a favorable precision efficiently.

In the case of the inkjet method, the liquid material applying unit includes nozzles capable of applying the liquid material to the layer of the powder material by the inkjet method. Nozzles of a known inkjet printer can be favorably used as the nozzles, and the inkjet printer can be favorably used as the liquid material applying unit. Preferable examples of the inkjet printer include SG7100 available from Ricoh Company, Ltd. The inkjet printer is preferable because the inkjet printer can realize rapid coating owing to the capability of dropping the liquid material from a head in a large amount at a time and obtaining a large coating coverage. In the present disclosure, the liquid material does not clog or corrode the nozzles or heads of the nozzles of an inkjet printer because the liquid material is free of solid matters such as particles and polymeric high-viscosity materials such as resins. Therefore, there are advantages that use of an inkjet printer capable of applying the liquid material precisely and highly efficiently provides an excellent object production efficiency, and that a hardened product having a favorable dimensional precision can be obtained easily, in a short time, and efficiently because, for example, unexpected volume increase will not occur because there are no polymeric components such as resins to be applied.

<Sintering Step and Sintering Unit>

The sintering step is a step of sintering a three-dimensional object formed by sequentially repeating the layer forming step and the liquid material applying step, and is performed by the sintering unit. Through the sintering step, the hardened product can be made into an integrated compact (sintered body). Examples of the sintering unit include a known sintering furnace.

As the sintering step, there is a method for performing sintering at same time as laminating layers of the powder material, as well as a method for sintering a hardened product after the hardened product is obtained as described above.

The method for performing sintering at the same time as laminating layers of the powder material is a method for irradiating the layers of the powder material with either a laser or an electron beam to sinter the layers of the powder material.

Laser Irradiation

The laser in the laser irradiation is not particularly limited and may be appropriately selected depending on the intended purpose. Examples of the laser include a $CO_2$ laser, an Nd-YAG laser, a fiber laser, and a semiconductor laser.

The conditions for the laser irradiation are not particularly limited and may be appropriately selected depending on the intended purpose. For example, when a compact laser is used, the compact laser is incapable of melting the powder material. Therefore, to form an object, it is preferable to mix an adhesive (for example, a polyester-based adhesive) to be used in combination and melt the adhesive by laser irradiation. In this case, it is preferable to use a $CO_2$ laser. Preferable irradiation conditions include a laser output of 15 W, a wavelength of 10.6 micrometers, and a beam diameter of about 0.4 mm.

Electron Beam Irradiation

The electron beam is not particularly limited except that an electron beam for irradiation has an energy by which the powder material can be melted, and may be appropriately selected depending on the intended purpose. For electron beam irradiation, there is a need for handling the powder material under a vacuum environment.

The conditions for the electron beam irradiation are not particularly limited and may be appropriately selected depending on the intended purpose. For example, an output of 1,500 W, a beam diameter of 0.1 mm, and a degree of vacuum of about $1.0 \times 10^{-5}$ mbar are preferable.

<Other Steps and Other Units>

Examples of the other steps include a drying step, a surface protection treatment step, and a painting step.

Examples of the other units include a drying unit, a surface protection treatment unit, and a painting unit.

Drying Step and Drying Unit

The drying step is a step of drying a hardened product obtained in the liquid material applying step, and is performed by a drying unit. In the drying step, an organic substance contained in the hardened product may also be removed (dewaxed), as well as the moisture. Examples of the drying unit include a known dryer.

Surface Protection Treatment Step and Surface Protection Treatment Unit

The surface protection treatment step is a step of forming a protective layer on the object formed in the liquid material applying step or the sintering step. Through the surface protection treatment step, the surface of the object can be provided with, for example, durability that enables the object to be subjected to, for example, use as is. Specific examples of the protective layer include a water-resistant layer, a weatherable layer, a light-resistant layer, a heat-insulating layer, and a gloss layer. Examples of the surface protection treatment unit include known surface protection treatment apparatuses such as a spray apparatus and a coating apparatus.

Painting Step and Painting Unit

The painting step is a step of painting the object. Through the painting step, the object can be colored in a desired color. Examples of the painting unit include known painting apparatuses such as painting apparatuses using, for example, a spray, a roller, and a brush.

Figure 1:
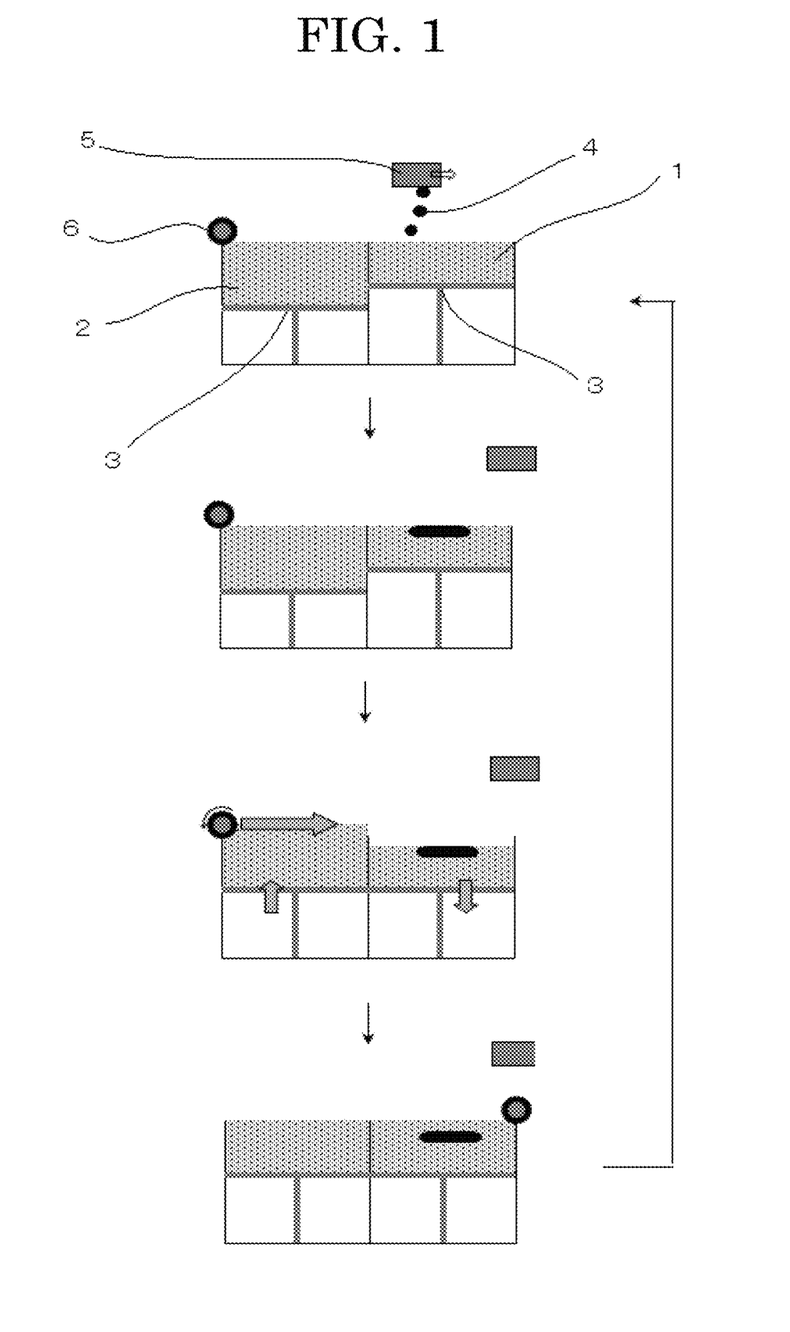
FIG. 1 is a schematic diagram illustrating an example of a powder additive manufacturing apparatus used in the present disclosure.

FIG. 1 illustrates an example of a powder additive manufacturing apparatus used in the present disclosure. The powder additive manufacturing apparatus of FIG. 1 includes a forming-side powder storing tank 1 and a supplying-side powder storing tank 2. Each of these powder storing tanks includes a stage 3 movable upward and downward. Layers of the powder material are formed on the stage.

Above the forming-side powder storing tank 1, there is provided an inkjet head 5 configured to discharge a liquid material 4 toward the powder material in the powder storing tank. Further, there is also provided a leveling mechanism 6 (hereinafter, may also be referred to as recoater) configured to supply the powder material from the supplying-side powder storing tank 2 to the forming-side powder storing tank 1 and level the surface of a layer of the powder material in the forming-side powder storing tank 1.

The liquid material 4 is dropped from the inkjet head 5 onto the powder material in the forming-side powder storing tank 1. Here, the position to which the liquid material 4 is dropped is determined based on two-dimensional image data (slice data) representing a plurality of planer layers into which a three-dimensional shape finally desired is sliced.

When printing on one layer is completed, the stage 3 of the supplying-side powder storing tank 2 is lifted up, and the stage 3 of the forming-side powder storing tank 1 is lifted down. This produces a height difference. An amount of the powder material corresponding to the height difference is moved to the forming-side powder storing tank 1 by the leveling mechanism 6.

In this way, a new layer of the powder material is formed on the surface of the powder material layer on which printing is performed before. The average thickness per layer of the powder material is about some tens of micrometers or greater but 100 micrometers or less.

Printing is performed on the layer of the powder material newly formed based on the slice data of the second layer. This series of process is repeated to obtain an object. The object is heated and dried by an unillustrated heating unit to obtain an object.

Figure 2:
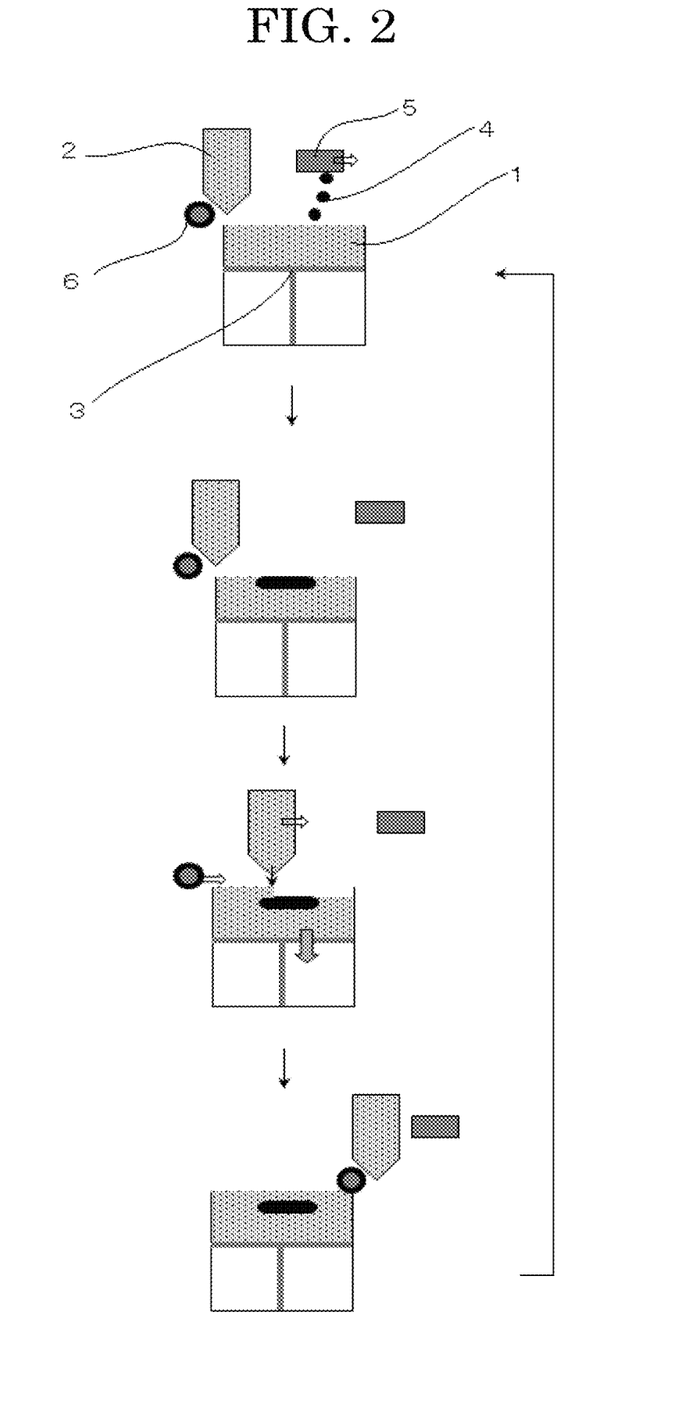
FIG. 2 is a schematic diagram illustrating another example of a powder additive manufacturing apparatus used in the present disclosure.

FIG. 2 illustrates another example of the powder additive manufacturing apparatus used in the present disclosure. The powder additive manufacturing apparatus of FIG. 2 is identical with FIG. 1 in principle but different in the mechanism of supplying the powder material. That is, the supplying-side powder storing tank 2 is disposed above the forming-side powder storing tank 1. When printing on one layer is completed, the stage 3 of the forming-side powder storing tank 1 lifts down by a predetermined amount, and the supplying-side powder storing tank 2 moves while dropping the powder material into the forming-side powder storing tank 1 in a predetermined amount, to form a new layer of the powder material. Subsequently, the leveling mechanism 6 compresses the layer of the powder material to increase the bulk density, and levels off the layer of the powder material to the uniform height.

The powder additive manufacturing apparatus having the configuration illustrated in FIG. 2 can be made smaller in size than the configuration of FIG. 1 in which two powder storing tanks are arranged horizontally.

<Three-Dimensional Object>

A three-dimensional object of the present disclosure is produced by the method for producing a three-dimensional object of the present disclosure.

It is preferable that the three-dimensional object be an artificial tooth because the three-dimensional object can endure a chewing force in an oral cavity for a long term and has an aesthetic property.

The artificial tooth is a tooth artificially made for recovering the function of a natural tooth that is lost due to, for example, dental caries, external injury, and periodontal disease. The artificial tooth encompasses a dental prosthesis such as a bridge and a crown.

The method and apparatus for producing a three-dimensional object of the present disclosure can produce an object having a complicated three-dimensional shape easily, efficiently, without a shape collapse before, for example, sintering, and with a favorable dimensional precision, using the powder material for forming a three-dimensional object of the present disclosure and the material set for forming a three-dimensional object of the present disclosure. The object (hardened product) obtained in this way rarely transforms into an unresolvable hydroxyapatite when transplanted in a living body, has no cytotoxicity, has a sufficient strength and an excellent dimensional precision, and can reproduce, for example, minute concavo-convexes and a curved surface. Therefore, the object (hardened product) has an excellent aesthetic appearance and a high quality, and can be favorably used for various applications.

EXAMPLES

The present disclosure will be described below by way of Examples. The present disclosure should not be construed as being limited to these Examples.

Preparation Example 1 of Granulated Particles

<Preparation of Powder Material 1 for Forming Three-Dimensional Object>

Synthesis of Inorganic Particles

An 18% by mass yttrium chloride aqueous solution was mixed with a 20% by mass zirconium oxychloride aqueous solution such that an yttria/zirconia equivalent ratio by mole would be 2.8/97.2. To the resultant, sodium chloride was added in an amount of 0.5% by mass of zirconium oxychloride and dissolved.

Next, to the obtained aqueous solution, aluminum chloride was added such that an amount as alumina would be 0.4% by mass of zirconia, and dissolved. The resultant aqueous solution was subjected to spray drying in the air having a temperature of 200 degrees C., to obtain a dry powder. The obtained dry powder was fired in the air at a temperature of 1,000 degrees C., to synthesize a calcined powder. The monoclinic rate of the obtained calcined powder was 15%. This calcined powder was pulverized with a wet attritor, to obtain a 30% by mass slurry.

Next, the obtained slurry was repeatedly subjected to dilution and filtration concentration with a membrane filter having a mesh size of 0.5 micrometers, and repeatedly washed until the electric conductivity of the filtrate became 20 microsiemens or lower. In the way described above, inorganic particles 1 were synthesized.

Granulation of Powder Material for Forming Three-Dimensional Object

Together with a polyacrylic acid having a weight average molecular weight Mw of 800,000 (PAA, available from Nippon Shokubai Co., Ltd., AS-58), the slurry after washed was subjected to spray drying for granulation with a spray dryer having an air temperature of 230 degrees C. at the inlet, to obtain a powder material 1 for forming a three-dimensional object containing the polyacrylic acid in an amount of 3% by mass.

Various properties of the inorganic particles 1 and the powder material 1 for forming a three-dimensional object obtained were evaluated in the manners described below. The results are presented in Table 1 to Table 3.

<Primary Particle Diameter of Inorganic Particles>

The particle diameter of the primary particles of the inorganic particles was measured with LA-920 (available from Horiba, Ltd.). In the measurement with LA-920, an application (Ver. 3.32) (available from Horiba, Ltd.) dedicated for LA-920 was used for an analysis. In the measurement with LA-920, specifically, background measurement was performed after optical axis adjustment was performed with chloroform. Subsequently, circulation was started, and the zirconia dispersion liquid was dropped. After it was confirmed that the transmittance had stabilized, ultrasonic irradiation was performed under the conditions described below. The dispersed particle diameter was measured on the condition that the transmittance after irradiation would fall within a range of 70% or higher but 95% or lower. What weighs in this measuring instrument is to perform measurement on the condition that the transmittance of the LA-920 would wall within a range of 70% or higher but 95% or lower in terms of measurement reproducibility of the particle diameter. Further, there is a need for performing measurement again when the transmittance after ultrasonic irradiation does not fall within the value. In order to obtain a transmittance value, there is a need for adjusting the amount of the dispersion liquid to be dropped. The conditions for measurement and analysis were set as follows.

[Conditions for Measurement and Analysis]
  Number of times of data acquisition: 15 times
  Relative refractive index: 1.20
  Circulation: 5
  Ultrasonic intensity: 7

<Contents of Zirconia, Yttrium, and Alumina in Inorganic Particles>

The contents of zirconia, yttria, and alumina in the inorganic particles were analyzed with an ICP emission spectrophotometer CIROS MARKII (available from Rigaku Corporation).

<Identification of Crystalline Phase of Inorganic Particles>

Identification of a crystalline phase of zirconia, which was the synthesized inorganic particles 1, was performed with an X-ray powder diffractometer (available from Rigaku Corporation, RINT 1100) under the conditions described above.

[Measurement Conditions]
  Tube: Cu
  Voltage: 40 kV
  Current: 40 mA
  Start angle: 3 degrees
  End angle: 80 degrees
  Scan speed: 0.5 degrees/min The monoclinic rate (%) of zirconia was calculated according to the formula (1) below based on the reflection peak intensities Im(111), Im(11-1), It(111), and Ic(111) of a 111 face and a 11-1 face of a monoclinic phase, a 111 face of a tetragonal phase, and a 111 face of a cubic phase by a powder X-ray diffractometry measurement.

$$\text{Monoclinic rate (\%)} = [Im(111) + Im(11\text{-}1)] / [Im(111) + Im(11\text{-}1) + It(111) + Ic(111)] \quad [\text{Formula (1)}]$$

<Volume Average Particle Diameter Dv of Powder Material for Forming Three-Dimensional Object>

COULTER MULTISIZER III (available from Coulter Counter, Inc.) was used as a measuring instrument. An interface configured to output number distribution and volume distribution (available from Japan Chemical Engineering & Machinery Co., Ltd.) was coupled to a personal computer. As an electrolytic solution, a 1% by mass NaCl aqueous solution was prepared with primary sodium chloride.

In the measuring method, to the aqueous solution serving as the electrolytic solution (from 100 mL through 150 mL), a surfactant (alkyl benzene sulfonate) serving as a dispersant (from 0.1 mL through 5 mL) was added, and the powder material for forming a three dimensional object (from 2 mg through 20 mg) was added. The resultant was subjected to dispersion treatment using an ultrasonic disperser for from 1 minute through 3 minutes. Further, the electrolytic aqueous solution (from 100 mL through 200 mL) was poured into another beaker, to which the sample dispersion liquid was added at a predetermined concentration. With COULTER MULTISIZER III, the average of 50,000 particles was measured using a 100 micrometer aperture as an aperture. The measurement was performed by dropping the dispersion liquid of the powder material for forming a three dimensional liquid such that the concentration indicated by the instrument became 8%±2%.

<Average Circularity of Powder Material for Forming Three-Dimensional Object>

The average circularity was measured with a flow-type particle image analyzer ("FPIA-3000", available from Sysmex Corporation) and analyzing software (FPIA-3000 DATA PROCESSING PROGRAM FOR FPIA VERSION 00-10). More specifically, a 10% by mass surfactant (alkyl benzene sulfonate, NEOGEN SC-A, available from DKS Co. Ltd.) (from 0.1 mL through 0.5 mL) was added to a 100 mL beaker formed of glass. To the resultant, the powder material for forming a three-dimensional object (from 0.1 g through 0.5 g) was added and mixed with a micro spatula. Next, to the resultant, ion-exchanged water (80 mL) was added. The obtained dispersion liquid was subjected to dispersion treatment using an ultrasonic disperser (available from Honda Electronics Co., Ltd.) for 3 minutes. Until the concentration in the dispersion liquid became from 5,000 particles/microliter through 15,000 particles/microliter, the shape and distribution of the powder material for forming a three-dimensional object were measured with FPIA-3000 mentioned above.

<Untamped Density of Powder Material for Forming Three-Dimensional Object>

The powder material for forming a three-dimensional object was filled in a 100 $cm^3$ container, leveled off, and weighed with a powder tester (available from Tsutsui Scientific Instruments Co., Ltd.). This operation was repeated 3 times, to obtain the average of the weight measurements. The average was divided by the volume of the container, to obtain the untamped density of the powder material for forming a three-dimensional object.

<BET Specific Surface Area of Powder Material for Forming Three-Dimensional Object>

Measurement was performed with an automatic specific surface area/micropore distribution measuring instrument (TRISTAR 3000, available from Shimadzu Corporation). A dedicated cell was filled with the powder material for forming a three-dimensional object (1 g), and deaerated with a degassing unit VACUPREP 061 (available from Shimadzu Corporation) dedicated for TRISTAR. The deaeration operation was performed at room temperature (25 degrees C.) at a reduced pressure of 100 mtorr or lower for 20 hours. Using the deaerated dedicated cell, the BET specific surface area was measured automatically with TRISTAR 3000 mentioned above. A nitrogen gas was used as an adsorption gas in the deaeration operation.

<Fluidity of Powder Material for Forming Three-Dimensional Object>

An apparatus including a supplying-side powder storing tank and a forming-side powder storing tank that were capable of moving upward and downward was made in house, and filled with the powder material for forming a three-dimensional object. Flatness of the surface of the powder after a roller configured to rotate in a counter direction was scanned was judged according to the criteria described below to evaluate fluidity. The roller was formed of SUS316 and moved over the powder material at a scanning speed of 100 mm/s at a rotational speed of 300 rpm.

[Evaluation Criteria]

A: A state that the surface became neatly flat.

B: A state that the surface became coarsely orange peel-like.

C: A state that the surface became coarsely grooved.

<Rate of Mass Reduction of Powder Material for Forming Three-Dimensional Object>

With a simultaneous thermogravimetric-differential thermal analyzer (available from SII Nanotechnology Inc., TG-DTA6200 EXSTAR6000), the rate of mass reduction (% by mass) from before to after the powder material for forming a three-dimensional object was heated to 1,000 degrees C. under a heating condition: 30 degrees C. to 600 degrees C., and at a heating rate of 10 degrees C./minute, and heated at 1,000 degrees C. for 1 hour was measured.

Preparation Example 2 of Granulated Particles

Preparation of Powder Material 2 for Forming Three-Dimensional Object

A powder material 2 for forming a three-dimensional object was produced in the same manner as in Preparation example 1 of granulated particles except that unlike in Preparation example 1, a polyacrylic acid having a weight average molecular weight Mw of 500,000 (available from Nippon Shokubai Co., Ltd.) was used instead. Various properties of the powder material 2 were evaluated. The results are presented in Table 1 to Table 3.

Preparation Example 3 of Granulated Particles

Preparation of Powder Material 3 for Forming Three-Dimensional Object

A powder material 3 for forming a three-dimensional object was produced in the same manner as in Preparation example 1 of granulated particles except that unlike in Preparation example 1, a polyacrylic acid having a weight average molecular weight Mw of 1,000,000 (available from Nippon Shokubai Co., Ltd.) was used instead. Various properties of the powder material 3 were evaluated. The results are presented in Table 1 to Table 3.

Preparation Example 4 of Granulated Particles

Preparation of Powder Material 4 for Forming Three-Dimensional Object

A powder material 4 for forming a three-dimensional object was produced in the same manner as in Preparation example 1 of granulated particles except that unlike in Preparation example 1, change was made to result in a polyacrylic acid content of 5% by mass. Various properties of the powder material 4 were evaluated. The results are presented in Table 1 to Table 3.

Preparation Example 5 of Granulated Particles

Preparation of Powder Material 5 for Forming Three-Dimensional Object

A powder material 5 for forming a three-dimensional object was produced in the same manner as in Preparation example 1 of granulated particles except that unlike in Preparation example 1, the mesh size of the membrane filter for dilution and filtration concentration of a calcined powder pulverized slurry during synthesis of inorganic particles was changed to 1.5 micrometers. Various properties of the powder material 5 were evaluated. The results are presented in Table 1 to Table 3.

Preparation Example 6 of Granulated Particles

Preparation of Powder Material 6 for Forming Three-Dimensional Object

A powder material 6 for forming a three-dimensional object was obtained by classifying the powder material 1 for forming a three-dimensional object produced in Preparation example 1 of granulated particles, and cutting coarse particles with adjustment of air blow strength to a weak level. Various properties of the obtained powder material 6 for forming a three-dimensional object were evaluated in the same manners as in Preparation example 1. The results are presented in Table 1 to Table 3.

Preparation Example 7 of Granulated Particles

Preparation of Powder Material 7 for Forming Three-Dimensional Object

A powder material 7 for forming a three-dimensional object was obtained by classifying the powder material 1 for forming a three-dimensional object produced in Preparation example 1 of granulated particles, and cutting fine particles with adjustment of air blow strength to a strong level. Various properties of the obtained powder material 7 for forming a three-dimensional object were evaluated in the same manners as in Preparation example 1. The results are presented in Table 1 to Table 3.

Preparation Example 8 of Granulated Particles

Preparation of Powder Material 8 for Forming Three-Dimensional Object

A powder material 8 for forming a three-dimensional object was produced in the same manner as in Preparation example 1 of granulated particles except that unlike in Preparation example 1, the temperature for spray drying for granulation with a spray dryer during granulation of inorganic particles was lowered from 230 degrees C. to 200 degrees C. Various properties of the powder material 8 were evaluated. The results are presented in Table 1 to Table 3.

Preparation Example 9 of Granulated Particles

Preparation of Powder Material 9 for Forming Three-Dimensional Object

A powder material 9 for forming a three-dimensional object was produced in the same manner as in Preparation example 1 of granulated particles except that unlike in Preparation example 1, the temperature for spray drying for granulation with a spray dryer during granulation of inorganic particles was raised from 230 degrees C. to 250 degrees C. Various properties of the powder material 9 were evaluated. The results are presented in Table 1 to Table 3.

Preparation Example 10 of Granulated Particles

Preparation of Powder Material 10 for Forming Three-Dimensional Object

A powder material 10 for forming a three-dimensional object was obtained by classifying the powder material 1 for forming a three-dimensional object produced in Preparation example 1 of granulated particles, and cutting particles having higher average circularities with adjustment of air blow strength to a strong level. Various properties of the obtained powder material 10 for forming a three-dimensional object were evaluated in the same manners as in Preparation example 1. The results are presented in Table 1 to Table 3.

Preparation Example 11 of Granulated Particles

Preparation of Powder Material 11 for Forming Three-Dimensional Object

A powder material 11 for forming a three-dimensional object was obtained by classifying the powder material 1 for forming a three-dimensional object produced in Preparation example 1 of granulated particles, and cutting particles having lower untamped densities with adjustment of air blow strength to a weak level. Various properties of the obtained powder material 11 for forming a three-dimensional object were evaluated in the same manners as in Preparation example 1. The results are presented in Table 1 to Table 3.

Preparation Example 12 of Granulated Particles

Preparation of Powder Material 12 for Forming Three-Dimensional Object

A powder material 12 for forming a three-dimensional object was obtained by classifying the powder material 1 for forming a three-dimensional object produced in Preparation example 1 of granulated particles, and cutting particles having higher untamped densities with adjustment of air blow strength to a strong level. Various properties of the obtained powder material 12 for forming a three-dimensional object were evaluated in the same manners as in Preparation example 1. The results are presented in Table 1 to Table 3.

Preparation Example 13 of Granulated Particles

Preparation of Powder Material 13 for Forming Three-Dimensional Object

A powder material 13 for forming a three-dimensional object was produced in the same manner as in Preparation example 1 of granulated particles except that unlike in Preparation example 1, the polyacrylic acid (PAA) which was a resin for granulation of the powder material 1 for forming a three-dimensional object 1 was changed to a polyvinyl alcohol (PVA, with a weight average molecular weight Mw of 800,000). Various properties of the powder material 13 were evaluated. The results are presented in Table 1 to Table 3.

Preparation Example 14 of Granulated Particles

Preparation of Powder Material 14 for Forming Three-Dimensional Object

A powder material 14 for forming a three-dimensional object was obtained in the same manner as in Preparation example 1 of granulated particles, except that unlike in Preparation example 1, during synthesis of inorganic particles, an 18% by mass yttrium chloride aqueous solution was mixed with a 20% by mass zirconium oxychloride aqueous solution such that an yttria/zirconia equivalent ratio by mole would be 4.1/91.4 to reduce the amount of the zirconium oxychloride aqueous solution. Various properties of the obtained powder material 14 for forming a three-dimensional object were evaluated in the same manners as in Preparation example 1. The results are presented in Table 1 to Table 3.

Preparation Example 15 of Granulated Particles

Preparation of Powder Material 15 for Forming Three-Dimensional Object

A powder material 15 for forming a three-dimensional object was obtained in the same manner as in Preparation example 1 of granulated particles, except that unlike in Preparation example 1, during synthesis of inorganic particles, an 18% by mass yttrium chloride aqueous solution was mixed with a 20% by mass zirconium oxychloride aqueous solution such that an yttria/zirconia equivalent ratio by mole would be 2.1/94.3 to reduce the amount of the yttrium chloride aqueous solution. Various properties of the powder material 15 were evaluated. The results are presented in Table 1 to Table 3.

Preparation Example 16 of Granulated Particles

Preparation of Powder Material 16 for Forming Three-Dimensional Object

A powder material 16 for forming a three-dimensional object was obtained in the same manner as in Preparation example 1 of granulated particles, except that unlike in Preparation example 1, during synthesis of inorganic particles, an 18% by mass yttrium chloride aqueous solution was mixed with a 20% by mass zirconium oxychloride aqueous solution such that an yttria/zirconia equivalent ratio by mole would be 6.2/91.5 to increase the amount of the yttrium chloride aqueous solution. Various properties of the powder material 16 were evaluated. The results are presented in Table 1 to Table 3.

Preparation Example 17 of Granulated Particles

Preparation of Powder Material 17 for Forming Three-Dimensional Object

A powder material 17 for forming a three-dimensional object was produced in the same manner as in Preparation example 1 of granulated particles, except that unlike in Preparation example 1, during synthesis of inorganic particles, aluminum chloride was added such that an amount as alumina would be 3.0% by mass of zirconia to increase the content of alumina. Various properties of the powder material 17 were evaluated. The results are presented in Table 1 to Table 3.

Preparation Example 18 of Granulated Particles

Preparation of Powder Material 18 for Forming Three-Dimensional Object

A powder material 18 for forming a three-dimensional object was produced in the same manner as in Preparation example 1 of granulated particles, except that unlike in Preparation example 1, the mesh size of the membrane filter for dilution, filtration, and concentration of a calcined powder pulverized slurry during synthesis of inorganic particles was changed to 1.5 micrometers. Various properties of the powder material 18 were evaluated. The results are presented in Table 1 to Table 3.

Preparation Example 19 of Granulated Particles

Preparation of Powder Material 19 for Forming Three-Dimensional Object

A powder material 19 for forming a three-dimensional object was obtained by classifying the powder material 1 for forming a three-dimensional object produced in Preparation example 1 of granulated particles, and significantly cutting coarse particles with adjustment of air blow strength to a weak level. Various properties of the obtained powder material 19 for forming a three-dimensional object were evaluated in the same manners as in Preparation example 1. The results are presented in Table 1 to Table 3.

Preparation Example 20 of Granulated Particles

Preparation of Powder Material 20 for Forming Three-Dimensional Object

A powder material 20 for forming a three-dimensional object was obtained by classifying the powder material 1 for forming a three-dimensional object produced in Preparation example 1 of granulated particles, and significantly cutting fine particles with adjustment of air blow strength to a strong level. Various properties of the obtained powder material 20 for forming a three-dimensional object were evaluated in the same manners as in Preparation example 1. The results are presented in Table 1 to Table 3.

Preparation Example 21 of Granulated Particles

Preparation of Powder Material 21 for Forming Three-Dimensional Object

A powder material 21 for forming a three-dimensional object was produced in the same manner as in Preparation example 1 of granulated particles except that unlike in Preparation example 1, the temperature for spray drying for granulation with a spray dryer during granulation of inorganic particles was lowered from 230 degrees C. to 180 degrees C. Various properties of the powder material 21 were evaluated. The results are presented in Table 1 to Table 3.

Preparation Example 22 of Granulated Particles

Preparation of Powder Material 22 for Forming Three-Dimensional Object

A powder material 22 for forming a three-dimensional object was produced in the same manner as in Preparation example 1 of granulated particles except that unlike in Preparation example 1, the temperature for spray drying for granulation with a spray dryer during granulation of inorganic particles was raised from 230 degrees C. to 260 degrees C. Various properties of the powder material 22 were evaluated. The results are presented in Table 1 to Table 3.

Preparation Example 23 of Granulated Particles

Preparation of Powder Material 23 for Forming Three-Dimensional Object

A powder material 23 for forming a three-dimensional object was produced in the same manner as in Preparation example 1 of granulated particles, except that unlike in Preparation example 1, the polyacrylic acid (PAA), which was a resin for granulation of the powder material 1 for forming a three-dimensional object, was not added. Various properties of the powder material 23 were evaluated. The results were presented in Table 1 to Table 3.

Preparation Example 1 of Liquid Material

Preparation of Liquid Material for Forming Three-Dimensional Object

Water (94.5 parts by mass), polyethyleneimine having a weight average molecular weight Mw of 70,000 (available from Nippon Shokubai Co., Ltd., P-1000) (5 parts by mass), and a surfactant TWEEN 20 (available from Tokyo Chemical Industry Co., Ltd.) (0.5 parts by mass) were subjected to dispersion using a homomixer for 30 minutes, to prepare a liquid material 1 for forming a three-dimensional object.

Example 1

A three-dimensional object 1 was produced in the manner described below using the obtained powder material 1 for forming a three-dimensional object and liquid material 1 for forming a three-dimensional object, and a shape printing pattern having a size (70 mm in length and 12 mm in width).

(1) First, with a known powder additive manufacturing apparatus as illustrated in FIG. 1, the powder material 1 for forming a three-dimensional object was moved from the supplying-side powder storing tank to the forming-side powder storing tank, to form a thin layer of the powder material 1 for forming a three-dimensional object having an average thickness of 100 micrometers on the support.

(2) Next, with an inkjet printer (available from Ricoh Company, Ltd., SG7100), the liquid material 1 for forming a three-dimensional object was applied (discharged) from the nozzles onto the surface of the formed thin layer of the powder material 1 for forming a three-dimensional object, to harden the powder material 1 for forming a three-dimensional object.

(3) Next, the operations of (1) and (2) above were repeated until the total average thickness became a predetermined thickness of 3 mm, to sequentially laminate hardened thin layers of the powder material 1 for forming a three-dimensional object, to produce a three-dimensional object 1.

An excessive amount of the powder material for forming a three-dimensional object was removed from the obtained three-dimensional object 1 by air blowing. As a result, the three-dimensional object 1 did not undergo a shape collapse. The three-dimensional object 1 was excellent in strength and dimensional precision.

Next, dimensional precision of the obtained three-dimensional object 1 was evaluated according to the criteria described below. The result is presented in Table 4.

<Dimensional Precision>

C: The obtained three-dimensional object was in a state that the surface was distorted and severely warped.

B: The obtained three-dimensional object was in a state that the surface was slightly distorted and warped.

A: The obtained three-dimensional object was in a state that the surface was smooth, beautiful, and not warped.

(4) The three-dimensional object 1 obtained in (3) above was subjected to a sintering treatment in a sintering furnace under a vacuum condition at 1,300 degrees C. The sintered body of the three-dimensional object 1 was a completely integrated structure, and did not undergo, for example, breakage even when slammed on a hard floor.

Next, compression strength after sintering, and sinterability of the obtained sintered body of the three-dimensional object 1 were evaluated according to the criteria described below. The result is presented in Table 4.

<Compression Strength after Sintering>

Compression strength was evaluated according to a compression strength test based on the sample shape and measurement conditions described below. The tester used was AUTOGRAPH-AGS-J available from Shimadzu Corporation.

Sample Shape
 Diameter: 5 mm
 Height: from 6 mm through 7 mm
 Mass: from 0.16 g through 0.18 g
Conditions for Compression Strength Test (JIS R1608)
 Crosshead speed: 0.5 mm·s$^{-1}$
 Set load: 500 kN <Sinterability>

Sinterability of the three-dimensional object was evaluated according to the criteria described below based on the measurement result of the compression strength.

C: The compression strength was less than 400 MPa

B: The compression strength was 400 MPa or greater but less than 800 MPa

A: The compression strength was 800 MPa or greater.

Examples 2 to 17 and Comparative Examples 1 to 6

Three-dimensional objects were produced in the same manner as in Example 1 except that unlike in Example 1, the powder material for forming a three-dimensional object and the liquid material for forming a three-dimensional object were combined as presented in Table 1, and were evaluated. The results are presented in Table 4.

TABLE 1

| | Powder material No. for forming three-dimensional object | Liquid material No. for forming three-dimensional object | Primary particle diameter (nm) | Zirconia content (% by mass) | Yttria content (% by mass) | Alumina content (% by mass) | Monoclinic rate (%) |
|---|---|---|---|---|---|---|---|
| Ex. 1 | 1 | 1 | 300 | 95.6 | 3.2 | 0.9 | 15 |
| Ex. 2 | 2 | 1 | 300 | 95.6 | 3.2 | 0.9 | 15 |
| Ex. 3 | 3 | 1 | 300 | 95.6 | 3.2 | 0.9 | 15 |
| Ex. 4 | 4 | 1 | 300 | 95.6 | 3.2 | 0.9 | 15 |
| Ex. 5 | 5 | 1 | 1,000 | 95.2 | 3.4 | 1.1 | 18 |
| Ex. 6 | 6 | 1 | 300 | 95.6 | 3.2 | 0.9 | 15 |
| Ex. 7 | 7 | 1 | 300 | 95.6 | 3.2 | 0.9 | 15 |
| Ex. 8 | 8 | 1 | 300 | 95.6 | 3.2 | 0.9 | 15 |
| Ex. 9 | 9 | 1 | 300 | 95.6 | 3.2 | 0.9 | 15 |
| Ex. 10 | 10 | 1 | 300 | 95.6 | 3.2 | 0.9 | 15 |
| Ex. 11 | 11 | 1 | 300 | 95.6 | 3.2 | 0.9 | 15 |
| Ex. 12 | 12 | 1 | 300 | 95.6 | 3.2 | 0.9 | 15 |
| Ex. 13 | 13 | 1 | 300 | 95.6 | 3.2 | 0.9 | 15 |
| Ex. 14 | 14 | 1 | 300 | 90.0 | 4.0 | 0.8 | 18 |
| Ex. 15 | 15 | 1 | 300 | 94.8 | 2.0 | 1.3 | 16 |
| Ex. 16 | 16 | 1 | 300 | 91.6 | 6.0 | 1.0 | 14 |
| Ex. 17 | 17 | 1 | 300 | 92.3 | 3.1 | 3.0 | 15 |
| Comp. Ex. 1 | 18 | 1 | 1,100 | 95.3 | 3.4 | 0.6 | 21 |
| Comp. Ex. 2 | 19 | 1 | 300 | 95.6 | 3.2 | 0.9 | 15 |
| Comp. Ex. 3 | 20 | 1 | 300 | 95.6 | 3.2 | 0.9 | 15 |
| Comp. Ex. 4 | 21 | 1 | 300 | 95.6 | 3.2 | 0.9 | 15 |
| Comp. Ex. 5 | 22 | 1 | 300 | 95.6 | 3.2 | 0.9 | 15 |
| Comp. Ex. 6 | 23 | 1 | 300 | 95.6 | 3.2 | 0.9 | 15 |

TABLE 2

| | Resin | | | | |
|---|---|---|---|---|---|
| | Kind | Content (% by mass) | Weight average molecular weight Mw | Product name | Supplier name |
| Ex. 1 | PAA | 3 | 800,000 | AS-58 | Nippon Shokubai Co., Ltd. |
| Ex. 2 | PAA | 3 | 500,000 | — | — |
| Ex. 3 | PAA | 3 | 1,000,000 | — | — |
| Ex. 4 | PAA | 5 | 800,000 | AS-58 | Nippon Shokubai Co., Ltd. |
| Ex. 5 | PAA | 3 | 800,000 | AS-58 | Nippon Shokubai Co., Ltd. |
| Ex. 6 | PAA | 3 | 800,000 | AS-58 | Nippon Shokubai Co., Ltd. |
| Ex. 7 | PAA | 3 | 800,000 | AS-58 | Nippon Shokubai Co., Ltd. |
| Ex. 8 | PAA | 3 | 800,000 | AS-58 | Nippon Shokubai Co., Ltd. |
| Ex. 9 | PAA | 3 | 800,000 | AS-58 | Nippon Shokubai Co., Ltd. |
| Ex. 10 | PAA | 3 | 800,000 | AS-58 | Nippon Shokubai Co., Ltd. |
| Ex. 11 | PAA | 3 | 800,000 | AS-58 | Nippon Shokubai Co., Ltd. |
| Ex. 12 | PAA | 3 | 800,000 | AS-58 | Nippon Shokubai Co., Ltd. |
| Ex. 13 | PVA | 3 | 800,000 | — | — |
| Ex. 14 | PAA | 3 | 800,000 | AS-58 | Nippon Shokubai Co., Ltd. |
| Ex. 15 | PAA | 3 | 800,000 | AS-58 | Nippon Shokubai Co., Ltd. |
| Ex. 16 | PAA | 3 | 800,000 | AS-58 | Nippon Shokubai Co., Ltd. |
| Ex. 17 | PAA | 3 | 800,000 | AS-58 | Nippon Shokubai Co., Ltd. |
| Comp. Ex. 1 | PAA | 3 | 800,000 | AS-58 | Nippon Shokubai Co., Ltd. |
| Comp. Ex. 2 | PAA | 3 | 800,000 | AS-58 | Nippon Shokubai Co., Ltd. |
| Comp. Ex. 3 | PAA | 3 | 800,000 | AS-58 | Nippon Shokubai Co., Ltd. |
| Comp. Ex. 4 | PAA | 3 | 800,000 | AS-58 | Nippon Shokubai Co., Ltd. |
| Comp. Ex. 5 | PAA | 3 | 800,000 | AS-58 | Nippon Shokubai Co., Ltd. |
| Comp. Ex. 6 | Absent | 0 | — | — | — |

TABLE 3

Powder material for forming three-dimensional object (granulated particles)

| | Volume average particle diameter (micrometer) after granulation | Average circularity | Untamped density (g/cm$^3$) | BET specific surface area (m$^2$/g) | Fluidity | Rate of mass reduction (% by mass) |
|---|---|---|---|---|---|---|
| Ex. 1 | 50 | 0.985 | 1.20 | 6.8 | A | 3.11 |
| Ex. 2 | 52 | 0.986 | 1.20 | 6.9 | A | 3.16 |
| Ex. 3 | 52 | 0.985 | 1.20 | 6.9 | A | 3.06 |
| Ex. 4 | 51 | 0.981 | 1.10 | 7.0 | A | 5.08 |
| Ex. 5 | 54 | 0.972 | 1.20 | 6.7 | A | 3.05 |
| Ex. 6 | 10 | 0.990 | 1.26 | 7.2 | A | 3.12 |
| Ex. 7 | 70 | 0.978 | 1.11 | 6.8 | A | 3.01 |
| Ex. 8 | 41 | 0.988 | 1.12 | 6.0 | A | 3.03 |
| Ex. 9 | 62 | 0.979 | 1.28 | 8.0 | B | 3.09 |
| Ex. 10 | 66 | 0.960 | 1.24 | 6.8 | A | 3.10 |
| Ex. 11 | 44 | 0.982 | 1.00 | 6.9 | B | 3.14 |
| Ex. 12 | 46 | 0.984 | 1.40 | 6.9 | B | 3.11 |
| Ex. 13 | 53 | 0.987 | 1.31 | 6.8 | A | 3.06 |
| Ex. 14 | 50 | 0.985 | 1.21 | 6.9 | A | 3.12 |
| Ex. 15 | 51 | 0.986 | 1.19 | 6.8 | A | 3.05 |
| Ex. 16 | 50 | 0.984 | 1.21 | 7.0 | A | 3.10 |
| Ex. 17 | 50 | 0.982 | 1.17 | 6.7 | A | 3.11 |
| Comp. Ex. 1 | 56 | 0.971 | 1.16 | 6.6 | A | 3.15 |
| Comp. Ex. 2 | 9 | 0.991 | 1.04 | 7.2 | C | 3.04 |
| Comp. Ex. 3 | 71 | 0.976 | 1.26 | 6.7 | A | 3.08 |
| Comp. Ex. 4 | 50 | 0.985 | 1.30 | 5.9 | A | 3.05 |
| Comp. Ex. 5 | 53 | 0.982 | 1.36 | 8.1 | C | 3.11 |
| Comp. Ex. 6 | 49 | 0.986 | 1.20 | 7 | A | 0.09 |

TABLE 4

| | Power material No. for forming three-dimensional object | Liquid material No. for forming three-dimensional object | Three-dimensional object Compression strength after sintering (MPa) | Sinterability | Dimensional precision before sintering |
|---|---|---|---|---|---|
| Ex. 1 | 1 | 1 | 725 | A | A |
| Ex. 2 | 2 | 1 | 788 | A | A |
| Ex. 3 | 3 | 1 | 703 | A | A |
| Ex. 4 | 4 | 1 | 532 | A | A |
| Ex. 5 | 5 | 1 | 401 | B | B |
| Ex. 6 | 6 | 1 | 799 | A | B |
| Ex. 7 | 7 | 1 | 653 | A | B |
| Ex. 8 | 8 | 1 | 667 | A | B |
| Ex. 9 | 9 | 1 | 768 | A | B |
| Ex. 10 | 10 | 1 | 689 | A | A |
| Ex. 11 | 11 | 1 | 738 | A | B |
| Ex. 12 | 12 | 1 | 717 | A | B |
| Ex. 13 | 13 | 1 | 724 | A | A |
| Ex. 14 | 14 | 1 | 697 | A | A |
| Ex. 15 | 15 | 1 | 662 | A | A |
| Ex. 16 | 16 | 1 | 711 | A | A |
| Ex. 17 | 17 | 1 | 726 | A | A |
| Comp. Ex. 1 | 18 | 1 | 381 | C | B |
| Comp. Ex. 2 | 19 | 1 | 745 | A | C |
| Comp. Ex. 3 | 20 | 1 | 719 | A | C |
| Comp. Ex. 4 | 21 | 1 | 659 | A | C |
| Comp. Ex. 5 | 22 | 1 | 771 | A | C |
| Comp. Ex. 6 | 23 | 1 | — | — | C |

* In Table 4, "—" in Comparative Example 6 means that measurement was impossible.

Aspects of the present disclosure are as follows, for example

<1> A powder material for forming a three-dimensional object, the powder material including
granulated particles containing a resin and inorganic particles of which primary particles have a volume average particle diameter of 1 micrometer or less,
wherein the granulated particles have a volume average particle diameter of 10 micrometers or greater but 70 micrometers or less and a BET specific surface area of 6 $m^2/g$ or greater but 8 $m^2/g$ or less.

<2> The powder material for forming a three-dimensional object according to <1>,
wherein the granulated particles have an average circularity of 0.960 or greater.

<3> The powder material for forming a three-dimensional object according to <1> or <2>,
wherein the granulated particles have an untamped density of 1.00 $g/cm^3$ or greater but 1.40 $g/cm^3$ or less.

<4> The powder material for forming a three-dimensional object according to any one of <1> to <3>,
wherein a rate of mass reduction from before to after the granulated particles are heated at 1,000 degrees C. for 1 hour is 5% by mass or less.

<5> The powder material for forming a three-dimensional object according to any one of <1> to <4>,
wherein the resin is a water-soluble resin.

<6> The powder material for forming a three-dimensional object according to any one of <1> to <5>,
wherein the resin contains an acidic functional group.

<7> The powder material for forming a three-dimensional object according to any one of <1> to <6>,
wherein the resin is either a polyacrylic acid or a polyvinyl alcohol.

<8> The powder material for forming a three-dimensional object according to <7>,
wherein the polyacrylic acid has a weight average molecular weight Mw of 500,000 or greater but 1,000,000 or less.

<9> The powder material for forming a three-dimensional object according to any one of <1> to <8>,
wherein a content of zirconia in the inorganic particles is 90% by mass or greater.

<10> The powder material for forming a three-dimensional object according to any one of <1> to <9>,
wherein a content of yttria in the inorganic particles is 2% by mass or greater but 6% by mass or less.

<11> The powder material for forming a three-dimensional object according to any one of <1> to <10>,
wherein a content of alumina in the inorganic particles is 3% by mass or less.

<12> The powder material for forming a three-dimensional object according to any one of <1> to <11>,
wherein the powder material for forming a three-dimensional object is a powder material used for three-dimensional object formation of laminating layers each obtained by applying a liquid material for forming a three-dimensional object to a layer formed of the powder material for forming a three-dimensional object and hardening the layer, the liquid material containing an aqueous medium.

<13> A material set for forming a three-dimensional object, the material set including:
the powder material for forming a three-dimensional object according to any one of <1> to <12>; and
a liquid material for forming a three-dimensional object, the liquid material containing an aqueous medium.

<14> A method for producing a three-dimensional object, the method including at least
a layer forming step of forming a layer of the powder material for forming a three-dimensional object according to any one of <1> to <12> on a support, the layer having a predetermined thickness.

<15> The method for producing a three-dimensional object according to <14>, the method including
a liquid material applying step of applying a liquid material for forming a three-dimensional object to the layer of the powder material for forming a three-dimensional object, the liquid material containing an aqueous medium.

<16> The method for producing a three-dimensional object according to <15>, the method further including
a sintering step of sintering a three-dimensional object formed by sequentially repeating the layer forming step and the liquid material applying step.

<17> The method for producing a three-dimensional object according to <14>, the method including
a sintering step of irradiating the layer of the powder material for forming a three-dimensional object with a laser or an electron beam to sinter the layer of the powder material for forming a three-dimensional object.

<18> A three-dimensional object producing apparatus including at least a layer forming unit configured to form a layer of the powder material for forming a three-dimensional object according to any one of <1> to <12> on a support, the layer having a predetermined thickness.

<19> A three-dimensional object which is produced by the method for producing a three-dimensional object according to any one of <14> to <17>.

<20> The three-dimensional object according to <19>,
wherein the three-dimensional object is used as an artificial tooth.

What is claimed is:

1. A method for producing a three-dimensional object, the method comprising:
   forming a layer of a powder material suitable for forming a three-dimensional object on a support, to obtain a powder material layer having a predetermined thickness,
   wherein the powder material comprises
      granulated particles that comprise a resin and inorganic particles, comprising yttria and/or zirconia, of which primary particles have a volume average particle diameter of 1 micrometer or less,
      wherein the granulated particles have a volume average particle diameter of 10 micrometers or greater but 70 micrometers or less and a BET specific surface area of 6 $m^2/g$ or greater but 8 $m^2/g$ or less.

2. The method of claim 1, further comprising:
   applying a liquid material suitable for forming a three-dimensional object to the powder material layer,
   wherein the liquid material comprises an aqueous medium.

3. The method of claim 2, further comprising
   sintering a three-dimensional object formed by sequentially repeating the forming a layer and the applying a liquid material.

4. The method of claim 1, further comprising:
   irradiating the powder material layer with a laser or an electron beam to sinter the powder material layer.

5. The method of claim 3, further comprising: prior to the sintering, forming the three-dimensional object into an artificial tooth.

6. The method of claim 1, wherein the three-dimensional object is used as an artificial tooth.

7. The method of claim 1, wherein a content of zirconia in the inorganic particles is 90% by mass or greater.

8. The method of claim 7, wherein a content of the yttria in the inorganic particles is 2% by mass or greater but 6% by mass or less, and wherein a content of alumina in the inorganic particles is 3% by mass or less.

9. The method of claim 1, wherein the primary particles have a volume average particle diameter of 300 nm or less.

10. The method of claim 1, wherein the granulated particles have an average circularity of 0.96 or greater.

11. The method of claim 1, wherein the granulated particles have an untamped density of 1.00 $g/cm^3$ or greater but 1.40 $g/cm^3$ or less.

12. The method of claim 1, wherein a rate of mass reduction from before to after the granulated particles are heated at 1,000 degrees C. for 1 hour is 5% by mass or less.

13. The method of claim 1, wherein the resin comprises a water-soluble resin.

14. The method of claim 1, wherein the resin comprises an acidic functional group.

15. The method of claim 1, wherein the resin comprises either a polyacrylic acid or a polyvinyl alcohol.

16. The method of claim 15, wherein the polyacrylic acid is present and has a weight average molecular weight Mw of 500,000 or greater but 1,000,000 or less.

17. The method of claim 7, wherein a content of the yttria in the inorganic particles is 2% by mass or greater but 6% by mass or less, and/or
   wherein a content of alumina in the inorganic particles is 3% by mass or less.

18. The method of claim 1, wherein a content of yttria in the inorganic particles is 2% by mass or greater but 6% by mass or less.

19. The method of claim 1, wherein a content of alumina in the inorganic particles is 3% by mass or less.

20. The method of claim 1, wherein the powder material is suitable to form laminating layers each obtained by applying a liquid material onto a layer formed of the powder material and hardening the layer, wherein the liquid material comprises an aqueous medium.

* * * * *